United States Patent [19]

Matsushima et al.

[11] 4,259,530

[45] Mar. 31, 1981

[54] PROCESS FOR THE PRODUCTION OF ALDEHYDES BY HYDROFORMYLATION

[75] Inventors: Yoshihisa Matsushima; Tadamori Sakakibara; Katsumi Kaneko, all of Ooit; Shozo Wada, Zushi; Yoshio Ishii, Nagoya; Yukio Nagashima; Nobukazu Okamoto, both of Ooi, all of Japan

[73] Assignee: Toa Nenryo Kogyo Kabushiki Kaisha, Tokyo, Japan

[21] Appl. No.: 73,662

[22] Filed: Sep. 7, 1979

[30] Foreign Application Priority Data

Apr. 6, 1979 [JP] Japan .................................. 54-40994

[51] Int. Cl.$^3$ ............................................. C07C 45/50
[52] U.S. Cl. ................................................... 568/454
[58] Field of Search ................. 260/604 HF; 568/909, 568/454, 451

[56] References Cited

U.S. PATENT DOCUMENTS

| | | | |
|---|---|---|---|
| 3,459,780 | 8/1969 | Wilkinson | 260/604 HF |
| 3,527,809 | 9/1970 | Pruett et al. | 260/604 HF |
| 3,821,311 | 6/1974 | Hughes et al. | 260/604 HF |
| 3,939,188 | 2/1976 | McVicker | 260/604 HF |
| 3,946,082 | 3/1976 | McVicker | 260/604 HF |
| 3,954,877 | 5/1976 | Gipson | 260/604 HF |
| 4,052,461 | 10/1977 | Tinker | 260/599 |
| 4,148,830 | 4/1979 | Pruett et al. | 260/604 HF |

FOREIGN PATENT DOCUMENTS

| | | | |
|---|---|---|---|
| 992101 | 6/1971 | Canada | 260/604 HF |
| 1338225 | 11/1973 | United Kingdom | 260/604 HF |
| 1357735 | 6/1974 | United Kingdom | 260/604 HF |

OTHER PUBLICATIONS

Brown "J. Chem. Soc." (A) 1970, pp. 2753–2764.
North "J. Organometal. Chem." vol. 21, pp. 445–447, (1970).
Olivier et al. "Hydrocarbon Processing" (1970), pp. 112–114 (4).
Jap. Pub. 10730/70=Japan Parent 903,326.
Jap. Pub. 17572/78=GB patent 1,315,551.
Evans et al. "J. Chem. Soc. (A) (1968), pp. 2660–2665.
Evans et al. "Chem. Communication" No. 71 (1967), p. 305.
Evans et al. "Inorganic Synthesis" vol. 8, pp. 211–214 (1966).
Evans et al. "Inorganic Synthesis" vol. 11, pp. 99–101 (1968).
Baker "J. Chem. Soc." D (1970) (17), pp. 1077–1078. Eng.
Barlex "J. Organometallic Chem." 13 (No.2) (1972), pp. 425–430.
Steele et al. "J. Chem. Soc." (1972) (19), pp. 2161–2169.
Garrov et al. "Inorganic" vol. 15, No. 3 (1976), pp. 646–650.
Steele et al. "Inorg. Nucl. Chem. Letters" vol. 7, pp. 877–879 (1971) Pergamon Press.

*Primary Examiner*—Werren B. Lone
*Attorney, Agent, or Firm*—Rebecca Yablonsky

[57] ABSTRACT

In an oxo process wherein an olefin is caused to react with carbon monoxide and hydrogen, a rhodium catalyst is provided by carrying out the hydroformylation in the presence of a rhodium source and free mixed ligands comprising a tertiary organo phosphorus and tertiary organo arsenic in excess of the quantity required for coordination to the rhodium atom. For example, HRh(CO)(PPh$_3$)$_3$ with excess AsPh$_3$/PPh$_3$ may be used to give a high reaction rate and good selectivity to n-aldehyde.

8 Claims, No Drawings

PROCESS FOR THE PRODUCTION OF ALDEHYDES BY HYDROFORMYLATION

BACKGROUND OF THE INVENTION

1. Field of the Invention

This invention relates to a process for the production of aldehydes by the hydroformylation of olefins and, more particularly, it is concerned with an improved process for producing aldehydes by reacting olefins, carbon monoxide and hydrogen in the presence of rhodium-containing complex compound catalysts and free ligands.

2. Description of the Prior Art

Rhodium-phosphine type or rhodium-phosphite type complexes are known as catalysts for the hydroformylation of olefins and a number of studies have been made thereon, see for example Chem. Comm., 305 (1967) Apr. 12, 1967.

The stability of a rhodium catalyst is increased by modification with phosphine, arsine or stibine, which permits practicing the oxo reaction at a rather low pressure. According to Japanese Pat. No. 903326, straight chain-rich aldehydes are prepared at a low total pressure with a low partial pressure of carbon monoxide and a high partial pressure of hydrogen in the presence of a rhodium triaryl phosphine catalyst and a triaryl phosphine ligand in a large excess to the rhodium. However, this method has the disadvantage that the hydroformylation reaction rate of an olefin is markedly decreased because of using a ligand in a large excess to rhodium, and a considerable quantity of a paraffin is formed by the hydrogenation of the olefin ["Hydrocarbon Processing" (4) 112) (1970)] due to the reaction at a low total pressure with a low partial pressure of carbon monoxide and a high partial pressure of hydrogen.

Rhodium catalysts in combination with arsines or stibines instead of phosphines have been proposed, but the studies thereof have not been made so intensively because of their lower activity compared with tertiary phosphine-rhodium catalysts.

Applicants have proposed in their U.S. Ser. No. 073,664 filed on even date herewith based on Japanese Patent Applications No. 121456/78 and 121457/78, hydroformylation of an olefin using a rhodium complex containing both a tertiary organo phosphorus ligand and tertiary organo-arsenic ligand [H Rh(CO)(ligand)$_3$] which is an active species for the hydroformylation in the presence of excess mixed ligands of a tertiary organo phosphorus compound and tertiary organo arsenic compound. That is to say, in the hydrogormylation of an olefin, the reaction rate is remarkably improved, the quantity of paraffin formed by the hydrogenation of the olefin is decreased and, in addition, the selectivity to normal chain aldehyde is kept similar or improved in comparison with carrying out the reaction in the presence of a tertiary organo phosphorus rhodium catalyst and excess tertiary organo phosphorus ligand. The said process is superior to the prior art from the viewpoint of efficiency of hydroformylation.

However, the present method has advantages with regard to the ease of preparing or providing the rhodium-mixed ligands catalyst of this invention.

SUMMARY OF THE INVENTION

The inventors have made studies of a catalyst system consisting of an easily synthesizable or available rhodium source, for example, an inorganic rhodium compound such as rhodium metal or rhodium oxide, a rhodium organic salt such as rhodium acetate, or a rhodium complex such as rhodium carbonyl, Rh (CO) (PPh$_3$)$_2$ Cl or HRh (CO) (PPh$_3$)$_3$ and excess mixed ligands of a tertiary organo phosphorus and tertiary organo arsenic and have found that when hydroformylation is carried out with this catalyst system, the effect of hydroformylation is equal to that of applicants' above-mentioned application. That is to say, the present invention relates to a process for producing aldehydes by reacting an olefin with carbon monoxide and hydrogen, the aldehydes having one more carbon atom than the olefin, which comprises carrying out the reaction in the presence of a rhodium source and free mixed ligands comprising a tertiary organo phosphorus and tertiary organo arsenic represented by the general formula XR$_3$ [wherein X represents phosphorus or arsenic and R represents an organo group, which may be same or different] in excess of the quantity required for coordination to the rhodium atom.

DETAILED DESCRIPTION

The easily obtainable or easily prepared rhodium source of the invention includes various rhodium compounds.

Examples are a rhodium metal such as rhodium black or supported rhodium, an inorganic rhodium compound such as rhodium oxide, rhodium nitrate, rhodium sulfate, rhodium chloride, rhodium bromide or rhodium iodide, a rhodium organic acid salt such as rhodium acetate or rhodium octoate, or a rhodium complex such as rhodium carbonyl, Rh(CO)$_2$(acac), Rh(CO)(acac)(PPh$_3$), Rh(CO)(PPh$_3$)$_2$ Cl, [Rh(CO)$_2$Cl]$_2$, HRh(CO)(PPh$_3$)$_3$, HRh(CO)(AsPh$_3$)$_3$, HRh(CO)[P(OPh)$_3$]$_3$, Rh(acac)$_3$, RhCl(PPh$_3$)$_3$, [RhCl(C$_2$H$_4$)$_2$]$_2$, [RhCl(1,5-COD)]$_2$, Rh(CO)(AsPh$_3$)$_2$Cl, Rh(NO)(PPh$_3$)$_3$, [(1,5-COD)Rh(PPh$_3$)$_2$] ClO$_4$ or [(1,5-COD)Rh(AsPh$_3$)$_2$] ClO$_4$ (wherein acac=acetylacetonate, Ph=phenyl and COD=cyclo octadienyl). Preferred examples from the viewpoint of commercial availability and ease of preparation are complex compounds such as HRh(CO)(PPh$_3$)$_3$, HRh(CO)(AsPh$_3$)$_3$, Rh(CO)$_2$(acac), [Rh(PPh$_3$)$_3$]$_2$, HRh(Ph$_2$PCH$_2$CH$_2$PPh$_2$)$_2$ and HRh(CO) [P(OPh)$_3$]$_3$.

The ligands (XR$_3$) used in the present invention are represented by the general formula PR$^1$R$^2$R$^3$ and As R$^4$R$^5$R$^6$ in which R$^1$ to R$^6$ represent alkyl, cycloalkyl, aryl, aralkyl, alkoxy, cycloalkoxy, aryloxy, and aralkyloxy groups and may be the same or different. Preferably, R$^1$, R$^2$, R$^3$, R$^4$, R$^5$ and R$^6$ are aryl groups and aryloxy groups and more preferably the same aryl group. In view of the reactivity and commercial availability, it is most preferably that they are all phenyl groups, that is, triphenyl phosphine and triphenyl arsine. The mixed ligands used in excess may be the same as or different from those contained in the rhodium complex, but the same ligands are advantageous commercially.

The sum of the amounts of mixed ligands may be chosen within a wide range. In general, the sum of the amounts of free mixed ligands is 3 mols or more per rhodium atom in the rhodium source. Since addition of free mixed ligands in too large an excess is disadvantageous with respect to the reaction and cost, the excess amount is preferably 5 to 1000 mols, most preferably 50 to 500 mols per rhodium atom.

The proportion of tertiary organo-phosphorus to tertiary organo arsenic used as mixed ligands in excess may be chosen within a wide range. This proportion is generally 5:1 to 1:5, preferably 2:1 to 1:3, in order to maintain the stability of the catalyst and show the effect of a mixed ligands system sufficiently.

The above mentioned rhodium source and mixed ligands are provided in a hydroformylation reactor in order to carry out the hydroformylation but the rhodium source may be contacted with a mixed gas of carbon monoxide and hydrogen in the presence of the mixed ligands in excess at an elevated pressure before the hydroformylation. In particular, a rhodium source containing halogen or rhodium nitrate is preferably treated with an alkaline reactant, e.g., aqueous sodium hydroxide, outside the reaction system under the above mentioned conditions.

It is known that the hydroformylation rate decreases with increasing mol ratio of a tertiary organo phosphorus to rhodium when carrying out the hydroformylation in the presence of a tertiary organo phosphorus-rhodium complex and a tertiary organo phosphorus in excess, see Journal of the Chemical Society (A) 1970, pp. 2753-2764.

On the other hand, in a hydroformylation in the presence of a tertiary organo phosphorus-rhodium complex and a tertiary organo arsenic in excess, decrease of the reaction rate is observed too, with increasing mol ratio of a tertiary organo arsenic to rhodium, and moreover, the rate is extremely slow and the selectivity to normal aldehyde is low compared with that in the tertiary organo phosphorus in excess.

The present invention shows the unique and commercially valuable result, which comprises not slowing down the rate of hydroformylation and not lowering the selectivity to n-butylaldehyde caused by the presence of a tertiary organo arsenic in excess, but maintaining the selectivity to normalbutylaldehyde and improving the reaction rate to 1.5 to 2 times that of the known process using tertiary phosphorus ligands.

Accordingly, a reactor can be reduced in size with the same output. Furthermore, it is possible to decrease the quantity of rhodium catalyst to olefin and the concentration of rhodium in a catalyst bed.

The quantity of a rhodium catalyst used in a hydroformylation, depending on the procedure and the variety of olefin used as a starting material, may be chosen—considering these conditions—within a wide range. In a catalyst recycling process wherein an olefin, synthesis gas and rhodium catalyst are fed to a reaction tower, the reaction mixture is withdrawn from the head of the tower, cooled and subjected to reduced pressure to separate a gaseous component, and the liquid product is passed through a distillation column to distill off the product and to give a still residue containing the rhodium catalyst which is then withdrawn from the bottom of the column and recirculated to the reaction tower, for example, the quantity of the rhodium catalyst is 10 ppm to 5% by weight, preferably 50 ppm to 1% by weight as rhodium atom based on olefin feed.

In a liquid fixed bed process wherein an olefin and synthesis gas are fed to a catalyst layer charged previously to a reaction tower and only the reaction product in the form of a mixture of gases and vapors is withdrawn from the top of the tower, the concentration of rhodium in the catalyst layer is generally 10 ppm to 5% by weight, preferably 50 ppm to 1% by weight.

The catalyst system of the present invention may be used batchwise in addition to the continuous procedures described above. The reaction conditions may be the same as those in the case of using the rhodium-tertiary organo phosphorus type catalysts. That is to say, the reaction temperature is ordinarily room temperature to 150° C., preferably 60° to 120° C., and the total pressure is ordinarily normal pressure to 100 atmospheres, preferably normal pressure to 50 atmospheres, most preferably normal pressure to 30 atmospheres. In addition, the hydrogen to carbon monoxide mol ratio in the reaction zone is 10/1 to 1/10, preferably 10/1 to 1/1. A solvent is not always indispensable, but in order to maintain stable operation, it is desirable to use a solvent.

The solvent may be chosen from a wide range among those having no detrimental influence on hydroformylation, for example, saturated hydrocarbons such as hexane, decane and dodecane; aromatic hydrocarbons such as benzene, toluene, xylene, cumene and diisopropylbenzene; and oxygen-containing compounds such as alcohols, ketones, esters, and preferably products and high boiling point by-products of hydroformylation.

The catalyst system of the present invention can be adapted to α-olefins such as ethylene, propylene, butene-1, hexene-1 and octene-1, olefins with internal double bonds such as butene-2 and octene-2, and vinyl compounds such as styrene, acrylonitrile, acrylic acid esters and allyl alcohols. The present catalyst system is most suitable for obtaining aldehydes rich in normal chain type isomers from α-olefins.

The present invention provides a commercially valuable process whereby in the hydroformylation of olefins, the reaction rate is increased, the quantity of paraffin by-product is decreased and, in addition, the selectivity to normal chain aldehyde is kept similar or improved in comparison with carrying out the reaction in the presence of a rhodium-tertiary organo phosphorus complex and excess tertiary organo phosphorus ligand in combination; and the greater ease of obtaining the catalyst and the similar effect on reaction rate, by-product and selectivity to normal aldehyde are shown in comparison with carrying out the reaction in the presence of a rhodium-tertiary organo phosphorus+tertiary organo arsenic complex and excess mixed ligands of tertiary organo phosphorus+tertiary organo arsenic ligand.

The following examples are given in order to illustrate the present invention in detail without limiting the same.

EXAMPLE 1

0.109 mmol of tris (triphenyl phosphine) rhodium carbonyl hydride [HRh(CO)(PPh$_3$)$_3$], 3.60 mmol of triphenyl phosphine, 3.60 mmol of triphenylarsine and 20 ml of n-dodecane were charged to a 300 ml stainless steel autoclave equipped with a magnetic stirrer which was purged with nitrogen. 5.0 g of propylene was introduced under pressure into the autoclave which was then heated to 110° C., an H$_2$/CO gas with a molar ratio of 1:1 was introduced and the reaction pressure was adjusted to 20 Kg/cm$^2$, followed by stirring. The synthesis gas was continuously supplied from a gas holder to keep the reaction pressure constant. After the reaction had been continued for 18 minutes, from the start until the conversion of propylene reached about 90%, the autoclave was cooled and the product was withdrawn and subjected to analysis by gas chromatography. The reaction rate measured by the pressure decrease of the synthesis gas in the gas holder was 11.1 ml/sec. The conversion of propylene was 89.3% and the ratio of normal isomer to branched isomer of butylaldehyde was 3.1. The yield of propane was 0.4%.

EXAMPLES 2 to 9 and COMPARATIVE EXAMPLES 1 to 6

Hydroformylations were carried out in a manner analogous to Example 1 except that the ratio of $PPh_3$/rhodium and $AsPh_3$/rhodium, reaction temperature and the mol ratio of $H_2/CO$ were varied, thus obtaining the results shown in the following Table.

As can be seen from these results, in the catalyst system containing mixed excess $PPh_3$ and $AsPh_3$, the reaction rate is increased to about 1.5 to 2 times that in the catalyst system containing excess $PPh_3$ only and the quantity of propane formed is somewhat decreased.

EXAMPLE 10 and COMPARATIVE EXAMPLE 7 et al. J. Organometal Chem., 21 445 (1970)]. Hydroformylations were carried out in a manner analogous to Example 1 except that this complex as rhodium source and mixed ligands of 5.45 mmol $PPh_3$ and 5.45 mmol $AsPh_3$ were used. The results are shown in the Table.

EXAMPLE 12

The hydroformylation of Example 1 was repeated except that a catalyst consisting of rhodium supported on activated carbon (Rh content: 1.0% by weight) and excess mixed ligands, was used.

COMPARATIVE EXAMPLE 8

The hydroformylation of Example 1 was repeated except that a catalyst of rhodium-mixed ligands and excess mixed ligands was used. It is apparent from the Table that the present invention and comparative Example 8 show a similar effect on activity and selectivity to normal chain aldehyde.

TABLE

| Ex. No. | Rhodium Source (0.109 mmol) | $PPh_3$/Rhodium Source (mol ratio) | $AsPh_3$/Rhodium Source (mol ratio) | $AsPh_3$/$PPh_3$ (mol ratio) | Reaction Temperature (°C.) | $H_2/CO$ (mol ratio) | Reaction Rate $-d(H_2/CO)/dt$ (ml/sec) | Propylene Conv. (ml/sec) | n/i of Butylaldehyde (mol Ratio) | Propane Yield (mol %) |
|---|---|---|---|---|---|---|---|---|---|---|
| 1 | $HRh(CO)(PPh_3)_3$ | 33 | 33 | 1.0 | 110 | 1/1 | 11.1 | 89.3 | 3.1 | 0.4 |
| 2 | " | 33 | 67 | 2.0 | " | " | 12.8 | 90.2 | 3.3 | 0.4 |
| 3 | " | 50 | 50 | 1.0 | " | " | 8.4 | 87.2 | 3.5 | 0.3 |
| 4 | " | " | 75 | 1.5 | " | " | 8.6 | 89.8 | 3.6 | 0.4 |
| 5 | " | " | 150 | 3.0 | " | " | 6.9 | 87.2 | 3.8 | 0.4 |
| 6 | " | 100 | 50 | 0.5 | " | " | 5.8 | 87.3 | 4.3 | 0.3 |
| 7 | " | " | " | " | 100 | " | 3.2 | 93.9 | 4.3 | 0.2 |
| 8 | " | " | " | " | 110 | 5/1 | 7.5 | 90.4 | 7.9 | 1.9 |
| 9 | " | 67 | 33 | " | " | 1.0 | 4.4 | 82.3 | 3.6 | 0.2 |
| 1* | $HRh(CO)PPh_3)_3$ | 33 | — | — | 110 | 1/1 | 5.8 | 89.6 | 2.7 | 0.7 |
| 2* | " | 50 | — | — | " | " | 5.6 | 90.9 | 2.9 | 0.7 |
| 3* | " | 100 | — | — | " | " | 4.0 | 90.2 | 4.0 | 0.5 |
| 4* | " | 200 | — | — | " | " | 2.5 | 88.7 | 5.2 | 0.4 |
| 5* | " | 100 | — | — | 100 | " | 2.3 | 87.1 | 4.0 | 0.5 |
| 6* | " | 100 | — | — | 110 | 5/1 | 5.5 | 90.4 | 6.6 | 2.3 |
| 10 | $HRh(CO)(AsPh_3)_3$ | 50 | 50 | 1.0 | 110 | 1/1 | 7.9 | 90.7 | 3.3 | 0.3 |
| 7* | " | — | " | — | " | " | 1.0 | 49.8 | 1.7 | 0.3 |
| 11 | $Rh(CO)_2(acac)$ | 50 | " | 1.0 | " | " | 7.6 | 86.5 | 3.4 | 0.4 |
| 12 | Rh/C(Rh 1.0 wt. %) | 67 | 33 | 0.5 | 110 | 1/1 | 6.0 | 88.2 | 3.8 | 0.2 |
| 8* | $HRh(CO)(PPh_3)_2(AsPh_3)$ | 50 | 50 | 1.0 | 110 | 1/1 | 8.8 | 87.2 | 3.7 | 0.4 |

* = Comparative Example $RhCl(CO)(AsPh_3)_2$ which was synthesized from $RhCl_3.3H_2O$ by the known method [L. Vallarince, J. Chem. Soc., (A) 2287 (1966)] was reacted in the presence of $AsPh_3$ in excess, in ethanol solvent, and under a nitrogen atmosphere at 65° C. After the reaction, the mixture was cooled to about 0° C., and then an ethanol solution of $NaBH_4$ was added dropwise, thereby forming $HRh(CO)(AsPh_3)_3$.

Hydroformylations were carried out in a manner analogous to Example 1 except that the above mentioned complex as rhodium source and mixed excess ligands of 5.45 mmol $PPh_3$ and 5.45 mmol $AsPh_3$ were used. The results are shown in the Table with the results of comparative Example 7 carried out in the presence of $AsPh_3$ as the only excess ligand.

It is apparent from these results that in a $HRh(CO)(AsPh_3)_3$/$AsPh_3$ catalyst system, the activity and the selectivity to normal chain aldehyde are lower, but in a mixed ligands catalyst system, higher activity and higher selectivity are achieved.

EXAMPLE 11

$(Rh)(CO)_2(CH_3CO\ CH_2CO\ CH_3)$ was synthesized from $[Rh(CO)_2Cl]_2$ by the known method [B. E. North

What is claimed is:

1. A process for the production of aldehydes having one more carbon atom than the starting α-olefin by reacting an α-monoolefin of 2-8 carbon atoms with hydrogen and carbon monoxide, which comprises carrying out the reaction at temperatures in the range of 60° to 120° C. and pressures in the range of 1 to 30 atmospheres in the presence of a rhodium source and free mixed ligands comprising triphenyl phosphine and triphenyl arsine in excess of the quantity required for coordination to the rhodium atom, the excess of total mixed ligands being 50 to 500 mols per gram atom rhodium, the mol ratio of triphenyl arsine to triphenyl phosphine being from 0.5 to 3.0.

2. A process according to claim 1 in which the rhodium source is selected from the group consisting of rhodium metal, an inorganic rhodium compound, a rhodium salt of an organic acid and a rhodium complex containing any of the following ligands:
(a) CO
(b) acetylacetonate
(c) cyclooctadienyl
(d) tertiary organo phosphorus (e) tertiary organo arsenic and mixtures of any of the above ligands except (d) with (e).

3. A process according to claim 2 in which the rhodium source is selected from the group consisting of:

HRh(CO)(PPh$_3$)$_3$

HRh(CO)(AsPh$_3$)$_3$

Rh(CO)$_2$(acac)

[Rh(PPh$_3$)$_3$]$_2$

HRh(Ph$_2$PCH$_2$CH$_2$PPh$_2$)$_2$

HRh(CO)[P(OPh)$_3$]$_3$

4. A process according to claim 3 in which the rhodium source is HRh(CO)(PPh$_3$)$_3$.

5. A process according to claim 3 in which the rhodium source is HRh(CO)(AsPh$_3$)$_3$.

6. A process according to claim 1 in which the AsPh$_3$/PPh$_3$ mol ratio is from 1:1 to 3:1.

7. A process according to claim 1 in which a solvent is present.

8. A process according to claim 7 in which the solvent is selected from the group consisting of saturated hydrocarbons, aromatic hydrocarbons, oxygen-containing compounds and hydroformylation products and by-products.

* * * * *